US011734601B2

(12) United States Patent
Birnbaum et al.

(10) Patent No.: US 11,734,601 B2
(45) Date of Patent: Aug. 22, 2023

(54) SYSTEMS AND METHODS FOR MODEL-ASSISTED COHORT SELECTION

(71) Applicant: Flatiron Health, Inc., New York, NY (US)

(72) Inventors: Benjamin Edward Birnbaum, Brooklyn, NY (US); Joshua Daniel Haimson, New York, NY (US); Lucy Dao-Ke He, New York, NY (US); Katharina Nicola Seidl-Rathkopf, Brooklyn, NY (US); Monica Nayan Agrawal, Atlanta, GA (US); Nathan Nussbaum, South Orange, NJ (US)

(73) Assignee: Flatiron Health, Inc., New York, NY (US)

( * ) Notice: Subject to any disclaimer, the term of this patent is extended or adjusted under 35 U.S.C. 154(b) by 1105 days.

(21) Appl. No.: 16/403,475

(22) Filed: May 3, 2019

(65) Prior Publication Data

US 2019/0258950 A1  Aug. 22, 2019

Related U.S. Application Data

(63) Continuation of application No. 15/951,614, filed on Apr. 12, 2018, now Pat. No. 10,304,000.

(Continued)

(51) Int. Cl.
*G06N 20/00* (2019.01)
*G06N 5/046* (2023.01)
(Continued)

(52) U.S. Cl.
CPC ............ *G06N 20/00* (2019.01); *G06N 5/046* (2013.01); *G16H 10/20* (2018.01); *G16H 10/60* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 2007/0174252 A1* | 7/2007 | Rawlings | ............... G06Q 10/10 |
| 2008/0082356 A1* | 4/2008 | Friedlander | ............ G16H 10/60 |
| | | | 702/19 |

(Continued)

OTHER PUBLICATIONS

International Search Report and Written Opinion of the International Searching Authority, in International Application No. PCT/US2018/027257, dated Jul. 23, 2018 (20 pages).

(Continued)

*Primary Examiner* — David R Vincent
(74) *Attorney, Agent, or Firm* — Finnegan, Henderson, Farabow, Garrett & Dunner, LLP

(57) ABSTRACT

Systems and methods are disclosed for selecting cohorts. In one implementation, a model-assisted selection system for identifying candidates for placement into a cohort includes a data interface and at least one processing device. The at least one processing device is programmed to access, via the data interface, a database from which feature vectors associated with an individual from among a population of individuals can be derived; derive, for the individual, one or more feature vectors from the database; provide the one or more feature vectors to a model; receive an output from the model; and determine whether the individual from among the population of individuals is a candidate for the cohort based on the output received from the model.

15 Claims, 7 Drawing Sheets

Related U.S. Application Data

(60) Provisional application No. 62/484,984, filed on Apr. 13, 2017.

(51) Int. Cl.
  *G16H 10/60* (2018.01)
  *G16H 10/20* (2018.01)
  *G16H 50/70* (2018.01)

(56) References Cited

U.S. PATENT DOCUMENTS

| | | | |
|---|---|---|---|
| 2009/0067756 A1* | 3/2009 | Meyer | G06V 10/98 382/310 |
| 2010/0312769 A1* | 12/2010 | Bailey | H04L 51/52 707/769 |
| 2012/0035954 A1 | 2/2012 | Yeskel | |
| 2012/0065987 A1 | 3/2012 | Farooq et al. | |
| 2013/0124224 A1 | 5/2013 | Srinivasan et al. | |
| 2013/0268532 A1 | 10/2013 | Doshi | |
| 2016/0148114 A1* | 5/2016 | Allen | G06N 5/02 706/11 |
| 2016/0300034 A1 | 10/2016 | Huddar et al. | |
| 2016/0379638 A1* | 12/2016 | Basye | G10L 15/22 704/235 |
| 2017/0140114 A1 | 5/2017 | Are et al. | |
| 2018/0107924 A1 | 4/2018 | Benson et al. | |

OTHER PUBLICATIONS

Office Action issued in Japanese Patent Application No. 2019-554553, dated May 12, 2022 (2 pages).

* cited by examiner

SYSTEMS AND METHODS FOR MODEL-ASSISTED COHORT SELECTION

CROSS REFERENCE TO RELATED APPLICATION

This application is a continuation of U.S. application Ser. No. 15/951,614, filed Apr. 12, 2018, which claims the benefit of priority of U.S. Provisional Application No. 62/484,984, filed on Apr. 13, 2017. The entire contents of the foregoing applications are incorporated herein by reference in their entirely.

BACKGROUND

Technical Field

The present disclosure relates to the selection of cohorts and, more specifically, to the use of one or more models to automatically select cohorts.

Background Information

Selection of cohorts can be time consuming and expensive. In some instances, cohorts in the medical area may be assembled by reviewing, through a process known as abstraction, the medical files and records associated with various patients (e.g., medical records) to determine which of the patients is a viable candidate for a particular cohort. Developing a cohort with a meaningful number of individuals, however, may require review of medical records associated with hundreds or thousands (or more) of patients, where each patient's history may include hundreds or thousands of pages of clinic notes, radiology reports, pathology reports, doctor or nurse observations, structured and unstructured data, and any other type of information that may be included in a patient's medical record (e.g., an electronic medical record (EMR) or other available data sources (e.g., claims data, patient-reported data)). Not only can such an abstraction process require significant amounts of time, but currently, it also often requires highly trained individuals capable of identifying in a patient's medical history those characteristics that may justify placement of an individual into a certain cohort. Thus, there is a need to not only reduce the time required for cohort selection, but also to reduce the costs associated with cohort selection by reducing the reliance on manual abstraction.

SUMMARY

Embodiments consistent with the present disclosure include systems and methods for selecting a cohort with the assistance of one or more models. Embodiments of the present disclosure may overcome one or more aspects of existing techniques for cohort selection by providing rule-based, automated techniques for cohort selection. For example, the rules may comprise explicit rules that relate features of a patient record to a probability of viability for a particular cohort or may comprise a portion of a machine learning model that transforms the features into the probability. The use of rules in accordance with embodiments of the present disclosure thus allows for faster and more efficient selection of candidates for a cohort than using extant techniques. In addition, the use of rules in accordance with embodiments of the present disclosure may be more accurate than extant techniques.

In one embodiment, a model-assisted selection system for identifying candidates for placement into a cohort includes a data interface and at least one processing device. The at least one processing device may be programmed to access, via the data interface, a database from which feature vectors associated with an individual from among a population of individuals can be derived; derive, for the individual, one or more feature vectors from the database; provide the one or more feature vectors to a model; receive an output from the model; and determine whether the individual from among the population of individuals is a candidate for the cohort based on the output received from the model.

In an embodiment, a method selects a cohort from among a population of individuals. The method includes accessing, via a data interface, a database from which feature vectors associated with an individual from among a population of individuals can be derived; deriving, for the individual, one or more feature vectors from the database; providing the one or more feature vectors to a model; receiving an output from the model; and determining whether the individual from among the population of individuals is a candidate for the cohort based on the output received from the model.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings.

DETAILED DESCRIPTION

Figure 1:
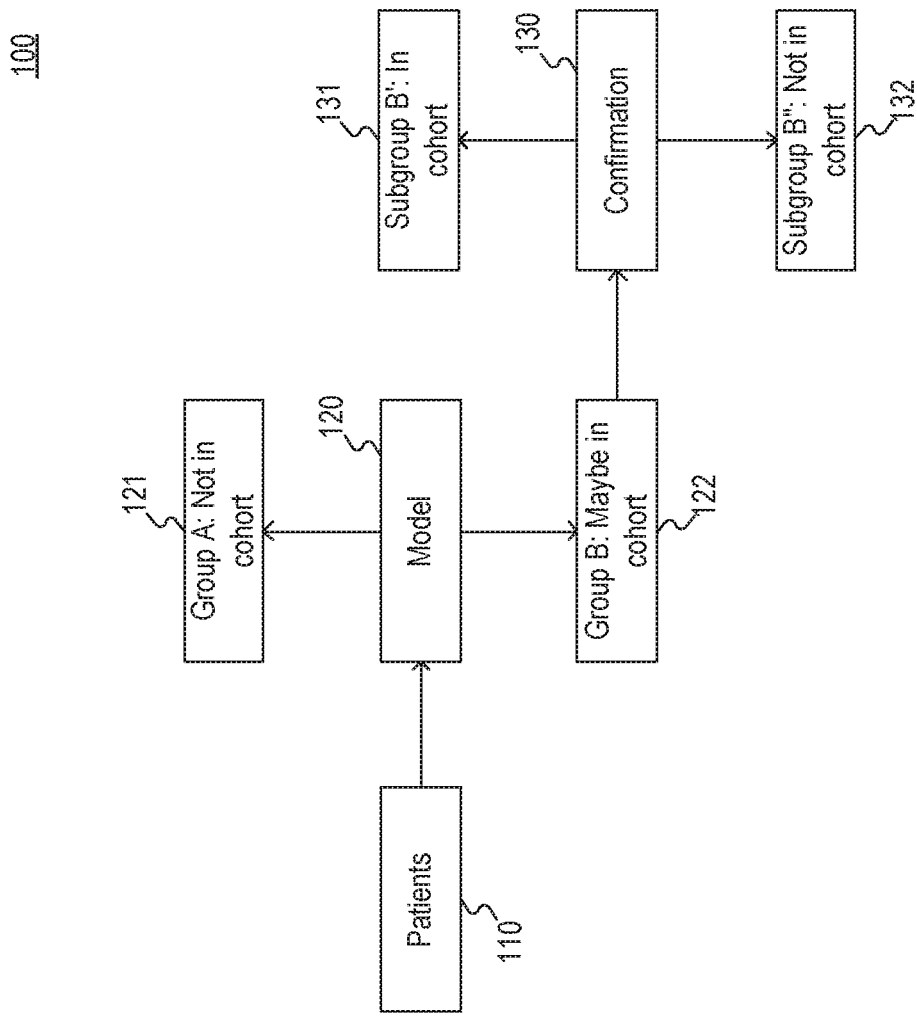
FIG. 1 is a block diagram illustrating a two-step cohort selection filter consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Embodiments of the present disclosure provide systems and methods for analyzing patient data and, in particular, selecting one or more cohorts. A user of the disclosed systems and methods may encompass any individual who may wish to access a patient's clinical experience and/or analyze patient data. Thus, throughout this disclosure, references to a "user" of the disclosed systems and methods may encompass any individual, such as a physician, a quality assurance department at a health care institution, and/or the patient.

FIG. 1 illustrates an exemplary two-step cohort selection filter 100. As depicted in FIG. 1, filter 100 may comprise a plurality of patients 110, a portion of which may be viable for inclusion in a cohort. For example, patients 110 may comprise a plurality of breast cancer patients, a portion of which may be metastatic, where metastatic status is an attribute relevant to cohort selection.

Patients 110 may be represented by a plurality of medical records. For example, each patient may be represented by one or more records generated by one or more health care professionals or by the patient. In such an example, a doctor associated with the patient, a nurse associated with the patient, a physical therapist associated with the patient, or the like, may each generate a medical record for the patient. In some embodiments, one or more records may be collated and/or stored in the same database. In other embodiments, one or more records may be distributed across a plurality of databases.

In some embodiments, the database may include a plurality of electronic data representations. For example, the patient records may be stored as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process.

As further depicted in FIG. 1, patients 110 are initially sorted by model 120. For example, model 120 may comprise one or more rules that identify characteristics of patients 110 based on associated medical records and use those characteristics to sort patients 110 into group 121 ("Not in cohort") and group 122 ("Maybe in cohort"). Examples of model 120 may include, but are not limited to, one or more machine learning models, such as the regressions and neural networks described in greater detail with respect to FIG. 4; an automated search for specific phrases combined with structured criteria (e.g., structured recordings of drug administrations) to determine which patients to select; application of rules to the output of natural language processing to determine which patients to select; or the like.

The patients sorted into group 122 may be further processed through confirmation 130. For example, confirmation 130 may comprise a separate model used to sort group 122 into subgroup 131 ("In cohort") and subgroup 132 ("Not in cohort"). Alternatively, confirmation 130 may comprise a manual sorting procedure performed by a medical expert.

As explained above, the use of model 120 to perform an initial sort allows for significant increases in efficiency in cohort selection at least because confirmation 130 is usually a costly and time-consuming process and model 120 reduces the number of patients input to confirmation 130. However, the use of automated rules and/or models in lieu of manual, subjective techniques introduces new technical problems. For example, automated rules or models that are over-inclusive fail to achieve significant improvements in efficiency in confirmation while imposing upfront costs to develop the automated rules or models. As another example, automated rules or models that are under-inclusive may fail to mitigate biases that inhere in manual, subject techniques. Accordingly, embodiments of the present disclosure include solutions to these technical problems of automated initial cohort sorting.

Figure 2A:
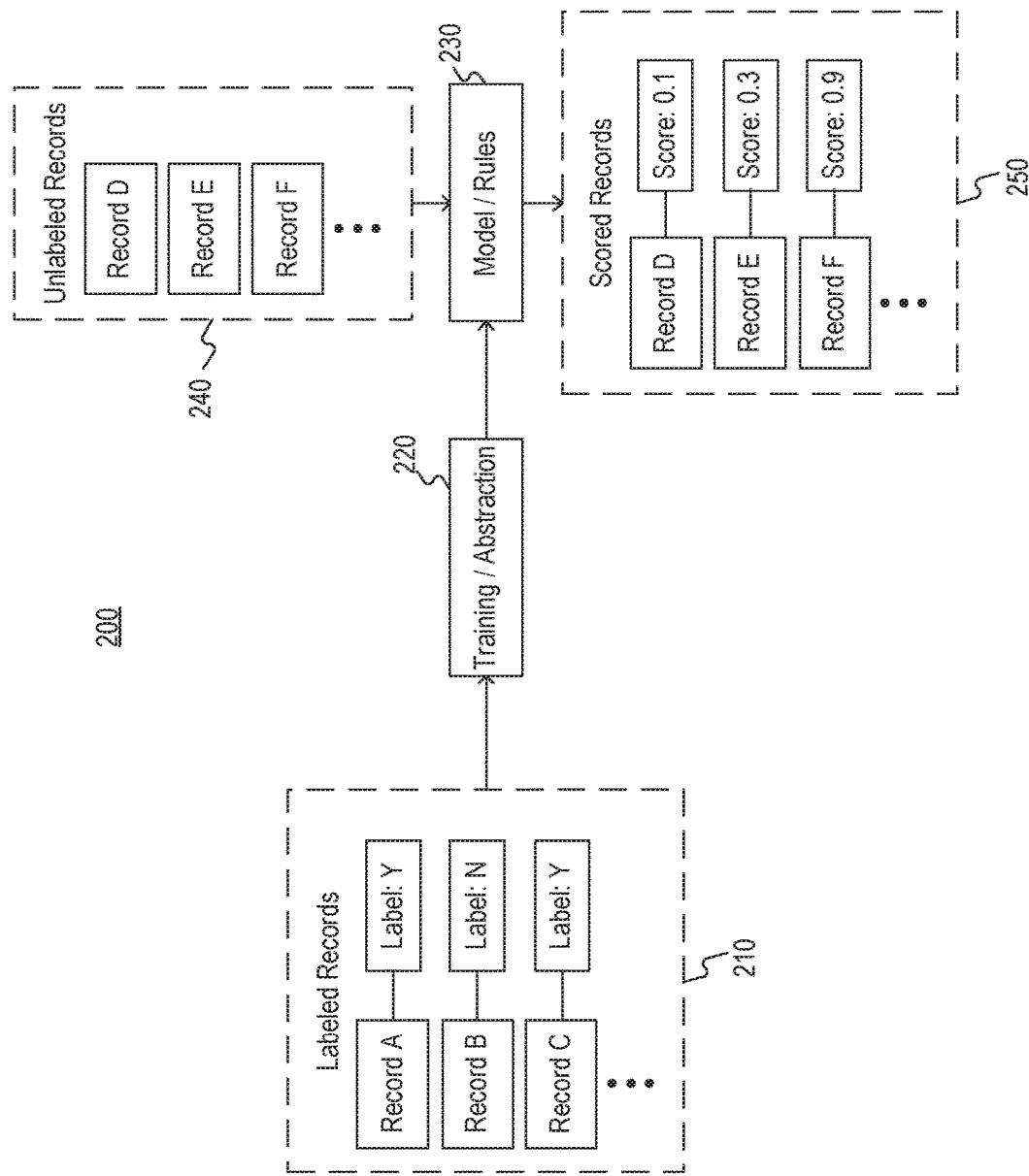
FIG. 2A is a block diagram illustrating a framework for a cohort selection model consistent with the present disclosure.

FIG. 2A illustrates a framework 200 for a cohort selection model. For example, framework 200 represents an example of an implementation of model 120 of filter 100 of FIG. 1.

As depicted in FIG. 2A, framework 200 may accept, as input, labeled records 210. For example, records 210 may include data associated with a plurality of patients such that each patient is associated with one or more medical records and is associated with a label. In such an example, the label may have been added by a medical professional. For example, the label may indicate whether the patient is suitable for inclusion in a cohort (e.g., by having one or more properties desired in the cohort, such as metastatic cancer).

As further depicted in FIG. 2A, framework 200 may input labeled records 210 to a training or abstraction process 220. Process 220 may extract one or more features (e.g., feature vectors or the like) from labeled records 210 to determine correlations between one set of features shared amongst patients labeled a first way and a second set of features shared amongst patients labeled a second way. The correlations need not be perfect—that is, one or more features in the set of features may be included in the records of one or more of the patients labeled in the second way and vice versa. In addition, the sets of features need not be fully shared amongst the associated patients—for example, one set of features may include one or more features only shared by a majority of patients labeled in the first way. The labels may, for example, indicate whether the patient is viable for a cohort.

Process 220 may therefore generate one or more models 230 based on the determined correlations. For example, as explained above, models 230 may comprise one or more rules relating features to probable labels, e.g., determined based on logistic regression, and/or one or more machine learned models, e.g., a neural network relating feature vectors to probable labels with associated likelihoods.

Once models 230 are constructed, unlabeled records 240 may be input to models 230. For example, records 240, like records 210, may include data associated with a plurality of patients such that each patient is associated with one or more medical records. Models 230 may extract features from unlabeled records 240 to produce scores associated with the unlabeled records 240. Therefore, each patient may have an associated score (e.g., 5 out of 10, 80% probability, 0.8 out of 1.0, "likely" on a scale from "not likely" to "somewhat likely" to "likely" to "very likely", or the like) indicating a likelihood that the patient is a viable candidate for a cohort.

Figure 2B:
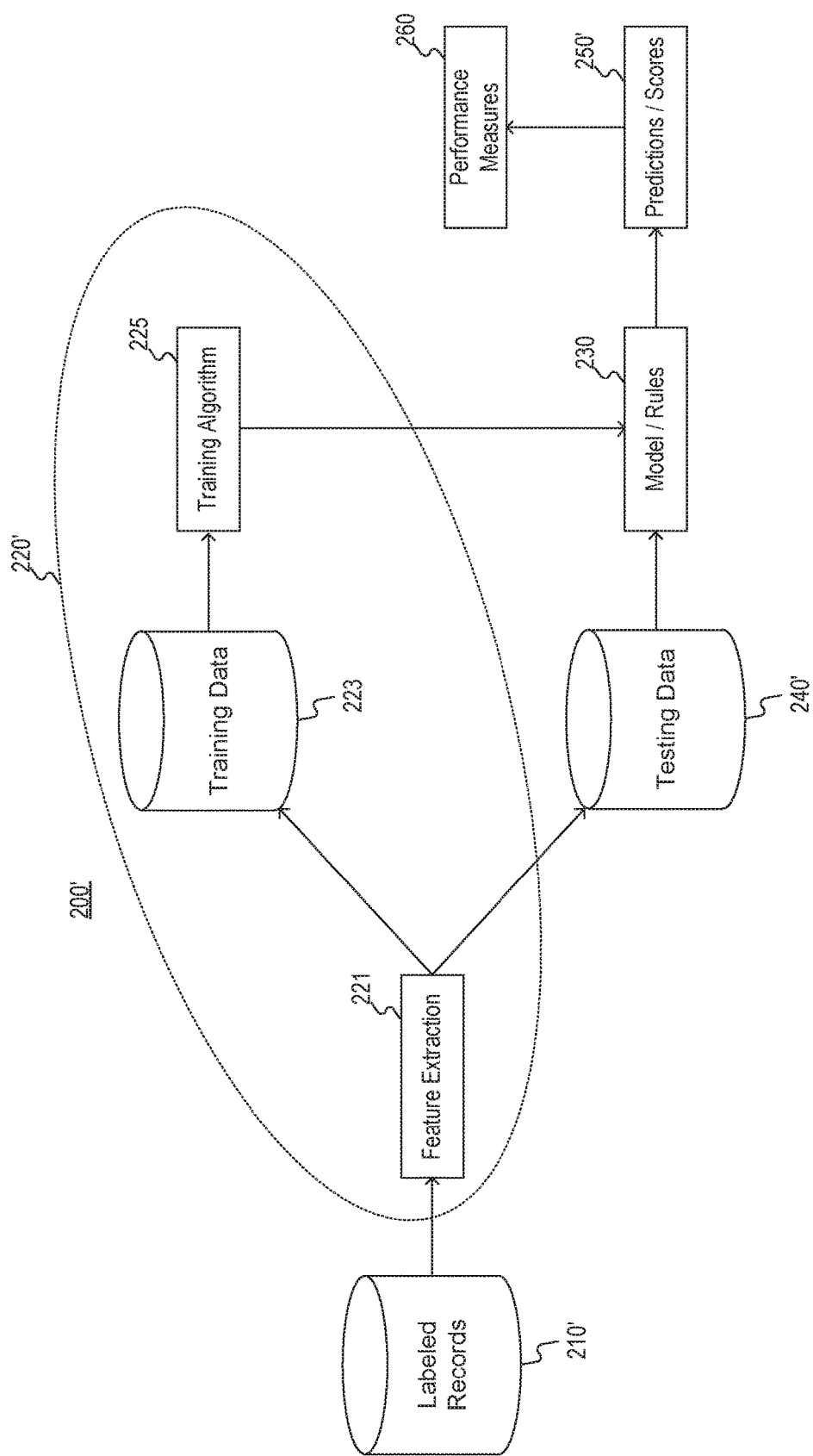
FIG. 2B is a block diagram illustrating a machine learning implementation of the framework of FIG. 2A.

FIG. 2B illustrates a machine learning implementation 200' of framework 200 of FIG. 2A. As depicted in FIG. 2B, labeled records 210' may be input to feature extraction 221. For example, labeled records 210' may be stored in one or more databases. Similar to unlabeled records 210, unlabeled records 210' may include data associated with a plurality of patients such that each patient is associated with one or more medical records.

Feature extraction 221 may extract features (such as key words, key phrases, or the like) from labeled records 210' and may score those features for a level of relevance to inclusion in a cohort. Accordingly, in some embodiments, the features may be represented as vectors.

A portion of the features extracted by feature extraction 221 may be collated with corresponding labels of records 210' and stored as training data 223. The collated data 223 may then be placed through a training algorithm 225. For example, training algorithm 225 may include logistic regression that generates one or more functions (or rules) that relate extracted features to particular labels. Additionally or alternatively, training algorithm 225 may include one or more neural networks that adjust weights of one or more nodes such that an input layer of features is run through one or more hidden layers and then through an output layer of labels (with associated probabilities). Accordingly, training algorithm 225 outputs one or more models 230.

The other portion of the features extracted by feature extraction 221 may be collated with corresponding labels of records 210' and stored as testing data 240'. Testing data 240' may be used to refine one or more models 230 to detect biases from under-inclusion or false positives from over-inclusion. The collated data 240' may then be placed through one or more models 230. One or more models 230 may produce predictions (or scores) 250' for testing data 240'. Performance measures 260 may be used to refine one or more models 230, e.g., by comparing predictions 250' to the labels of testing data 240'. For example, as explained above, one or more models 230 may be re-trained (e.g., modified) to reduce deviations between the labels and predictions 250'. The modifications may be based on one or more loss functions.

Figure 3A:
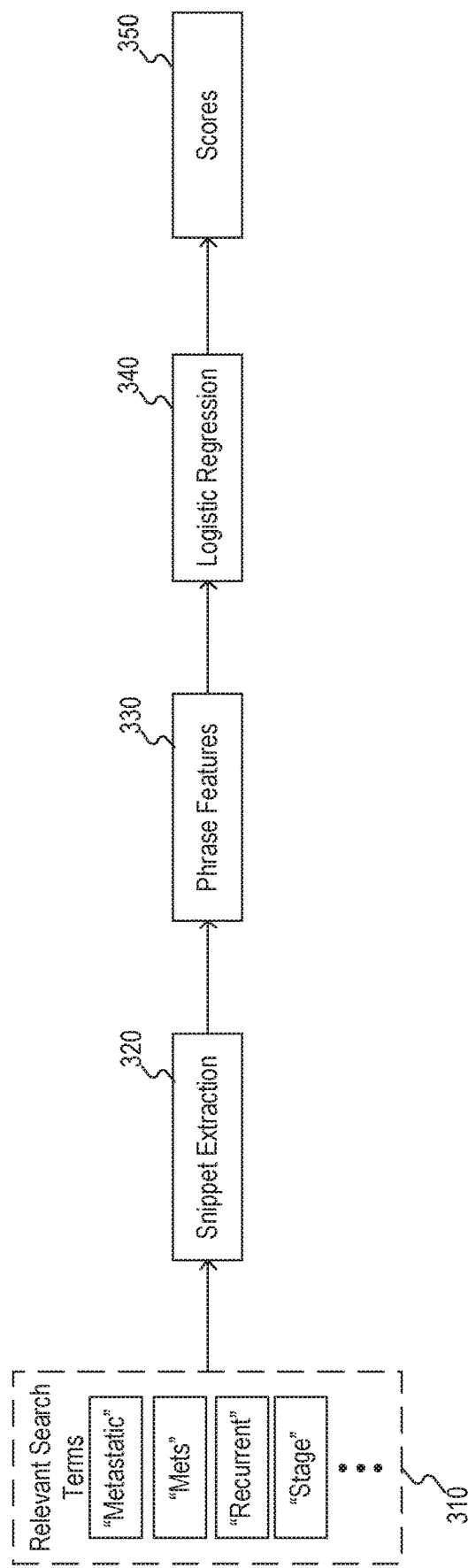
FIG. 3A is a block diagram illustrating an example technique for constructing a model from search terms consistent with the present disclosure.

FIG. 3A illustrates an example technique 300 for constructing a model from search terms. For example, technique 300 may be used to develop model 120 of FIG. 1.

As depicted in FIG. 3A, relevant search terms 310 may be selected for use in model construction. For example, the search terms 310 may be selected by health care professionals that are trained to perform manual, subjective selection of cohorts. Accordingly, search terms 310 may be input to snippet extraction 320. By assessing snippets surrounding relevant terms 310 rather than the relevant terms alone, the model may be trained to differentiate "metastatic" from "not metastatic"; "stage ii" from "stage iv"; or the like.

After snippet extraction 320, phrase features 330 may be determined based on the extracted snippets. In some embodiments, structured data included in medical records from which the snippets were extracted may also be assessed with the snippets. For example, the phrases extracted, as well as any structured data considered, may be converted into a multi-dimensional vector that correlates a score to the phrases and other structured data. The score for each phrase and/or portion of structured data may represent a magnitude along a dimension associated with the corresponding phrase and/or portion. In some embodiments, the score may be binary, such that the presence of a phrase results in a magnitude of 1 along the dimension associated with the phrase while the absence of a phrase results in a magnitude of 0 along the dimension associated with the phrase. For example, the vector may have a component magnitude of 1 along the "not metastatic" dimension if the extracted snippets include the phrase "not metastatic" and a component magnitude of 0 along the "metastatic" dimension if the extracted snippets only include the phrase "not metastatic" and not the phrase "metastatic" apart from the modifier "not." In other embodiments, the score may be non-binary and may indicate, for example, a prevalence associated with the phrase. For example, the vector may have a component magnitude of 5 along the "metastatic" dimension if the extracted snippets include five instances of the phrase "metastatic" and a component magnitude of 2 along the "not metastatic" dimension if the extracted snippets only two instances of the phrase "not metastatic." The prevalence may represent a normalized measure of instances, such as total instances per a particular number of characters, a particular number of words, a particular number of sentences, a particular number of paragraphs, a particular number of pages, or the like.

Phrase features 330 may be input into logistic regression 340 to determine scores based on phrase features 330. The scores may be correlated with or otherwise indicate suitability for inclusion in (and/or exclusion from) the cohort. In an alternative embodiment, phrase features 330 may be input into logistic regression 340 to determine the top features (not shown) correlated with inclusion in (and/or exclusion from) the cohort. The top features may then be used to develop one or more models, as explained above with respect to FIGS. 2A and 2B.

Figure 3B:
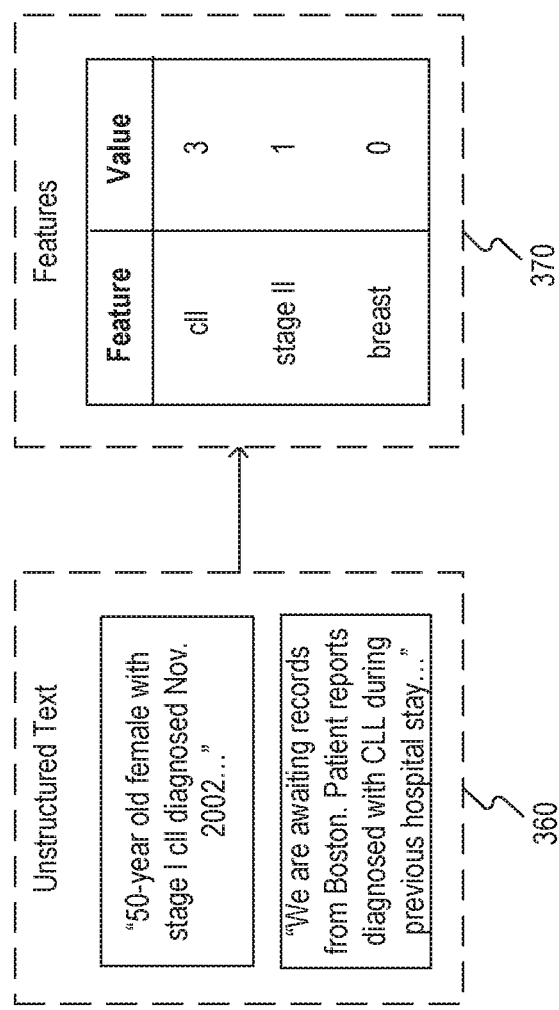
FIG. 3B is a block diagram illustrating an example of natural language processing on unstructured text consistent with the present disclosure.

FIG. 3B illustrates an example technique 300' of natural language processing on unstructured text. For example, technique 300' may be used in technique 300.

As depicted in FIG. 3B, unstructured text 360 may include, for example, notes included in one or more medical records associated with one or more patients. As used herein, "unstructured" refers to text that is not categorized into one or more standardized formats (e.g., a date format, a name format, or the like) and is not in a serialized or markup format (such as XML, YAML, JSON, or the like).

Unstructured text 360 may be used to extract features 370. For example, as explained above with respect to FIG. 3A, features 370 may be represented as vectors and may represent a measure of the particular phrase along one or more dimensions. Features 370 may comprise component vectors of a single multi-dimensional vector capturing features 370.

Figure 4:
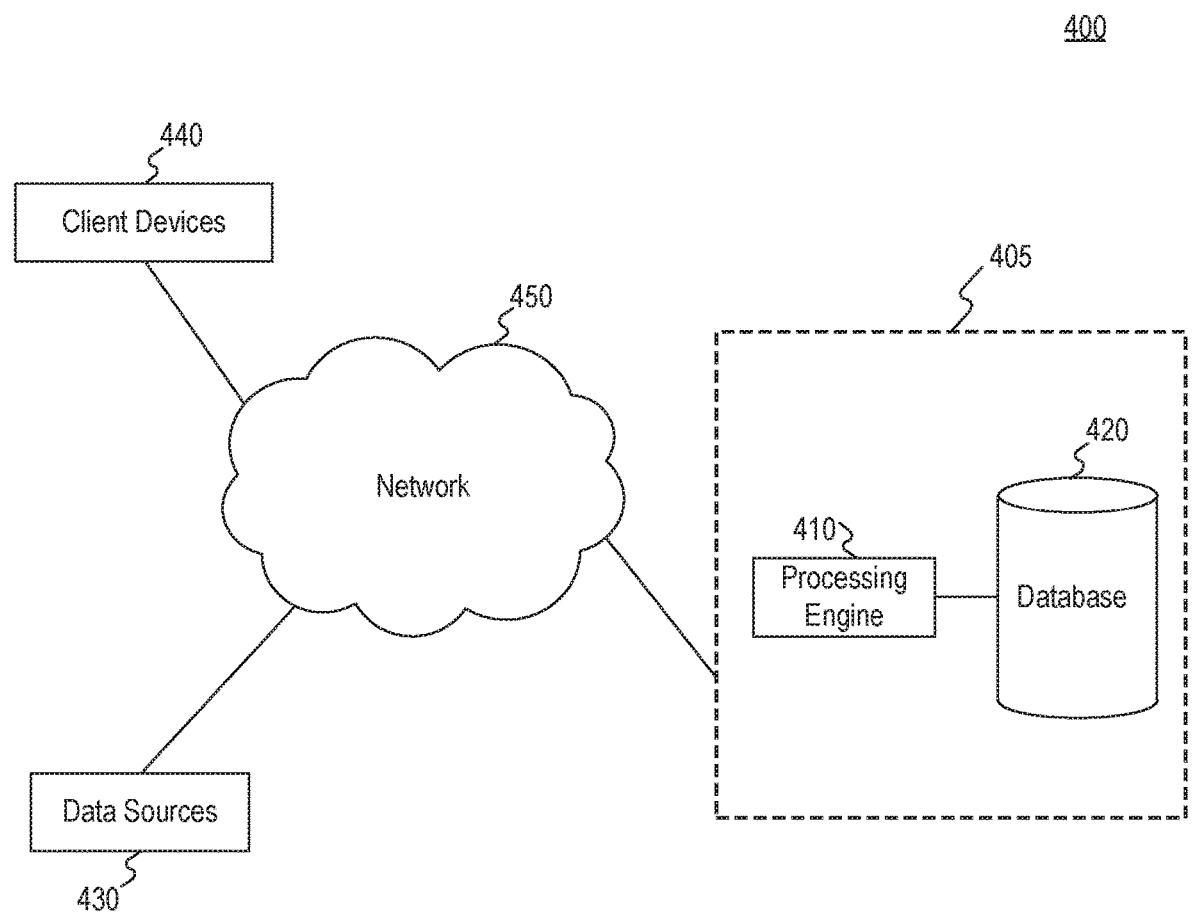
FIG. 4 is a block diagram illustrating an exemplary system environment for implementing embodiments consistent with the present disclosure.

FIG. 4 illustrates an exemplary system environment 400 for implementing embodiments of the present disclosure, such as method 500 of FIG. 5, described below. As shown in FIG. 4, system environment 400 includes several components. It will be appreciated from this disclosure that the number and arrangement of these components is exemplary and provided for purposes of illustration. Other arrangements and numbers of components may be utilized without departing from the teachings and embodiments of the present disclosure.

As shown in FIG. 4, the exemplary system environment 400 includes a system 405. System 405 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 405 may include a processing engine 410 and one or more databases 420, which are illustrated in a region bounded by a dashed line for system 405 in FIG. 4.

In one embodiment, system 405 may transmit and/or receive patient medical data to/from various other components, such as one or more data sources 430 and client devices 440. The medical data may be stored in one or more medical records, each medical record associated with a patient. More specifically, system 405 may be configured to receive and store the data transmitted over a network 450 (e.g., Internet, Intranet, WAN, LAN, cellular, etc.) from various data sources, including data sources 430, process the received data, and transmit search results based on the processing to client devices 440.

The various components of system environment 400 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

As described above, system 405 may be configured to receive patient medical records over a network 450, apply one or more models to the received medical results, and provide viability probabilities to client devices 440 over the network 450. For example, system 405 may receive patient medical records from data sources 430 or elsewhere on network 450. The records provided to system 405 from data sources 430 (or elsewhere) may include structured data, such as gender, birth year, race, visit date, practice type, insurance carrier and start date, office visits, medication orders, medication administrations, Eastern Cooperative Oncology Group (ECOG) performance status (i.e., ECOG score), weight, lab results, etc.; unstructured data, such as diagnosis date, first activity date, stage at diagnosis, advanced diagnosis date, metastatic diagnosis date (usually for cancer patients), biomarker results, tumor progression and response (usually for cancer patients), oral medications, and laboratory details regarding the lab tests, etc.; and derived data, such as date of death, lines of therapy, and last activity date, outcomes, etc. In one embodiment, the unstructured data may be captured by an abstraction process, while the structured data may be entered by the health care professional or calculated using algorithms. In one embodiment, data sources 430 may include medical care providers (e.g., physicians, hospitals), laboratories, insurance companies, and any other source of patient data.

System 405 may also communicate with client devices 440 over network 450. For example, client devices 430 may transmit queries for patient medical records over network 450 to system 405. In one embodiment, a query for the records may include patient characteristics, such as patient identifier (ID), biomarker status, stage, drug/line combination, lines of therapy, age range at advanced diagnosis, date of advanced diagnosis, an indicator from whence the test sample came, details on the actual Epidermal Growth Factor Receptor (EGFR) mutation, an indicator from whence the test tissue was collected (for cancer tests), type of assay, straining intensity, if metastasized and if spread (for cancer patients), etc. System 405 may query database 420 to identify one or more patients matching the query parameters and transmit medical records associated with the matching patient(s) over network 450 to client devices 440.

In accordance with certain embodiments, system 405 may include one or more processing engines 410, which may be configured to transmit medical records over network 450 to and from data sources 430 and client devices 440. In one embodiment, each processing engine 410 may store records received from data sources 430 and client devices 440 in one or more databases 420. Databases 420 may be any suitable combination of large scale data storage devices, which may optionally include any type or combination of slave databases, load balancers, dummy servers, firewalls, back-up databases, and/or any other desired database components. Each processing engine 410 may also access data stored by databases 420 to process queries received from client devices 440. For example, processing engine 410 may access from databases 420 patient data (e.g., patient medical records) received from data sources 430 and generate a user interface that visualizes the patient data (e.g., on a timeline) in a standardized format. Processing engine 410 may transmit the generated user interface to client device 440 for visualization of one or more patient records.

As discussed above, system 400 may exchange data, and such exchanges may occur over a data interface. As used herein, a data interface may include any boundary across which two or more components of system 400 exchange data. For example, system 400 may exchange data between software, hardware, databases, devices, humans, or any combination of the foregoing. Furthermore, it will be appreciated that any suitable configuration of software, processors, data storage devices, and networks may be selected to implement the components of system environment 400 and features of related embodiments.

In some embodiments, system 405 may select one or more cohorts. As used herein, a cohort may include any grouping of data (people, articles, objects, etc.) that shares at least one common characteristic or that exhibit attributes meeting a predefined set of criteria. In some embodiments, a cohort may include individuals that exhibit at least one common characteristic from a medical perspective (e.g., demographic or clinical characteristics). An individual may include any member of one or more groups (e.g., objects, people, articles, etc.). For example, those individuals from a population determined to have a certain type of disease, or more specifically, certain characteristics associated with that disease (e.g., breast cancer in stage IV) may be identified and placed in a common cohort. Cohorts may be assembled for various purposes. In some instances, cohorts may be assembled to form groups used to analyze the characteristics of certain diseases, such as their epidemiology, treatment approaches, how outcomes such as mortality or progression of disease depend on certain variables, or the like.

As discussed earlier, selection of cohorts may be time consuming and expensive for a variety of reasons. For example, an abstraction process for selecting cohorts may require significant amounts of time, and often requires highly trained individuals capable of identifying in a patient's medical history those characteristics that may justify placement of an individual into a certain cohort. Moreover, effective abstraction requires highly trained abstractors that can exercise good judgment in cohort selection. This subjective process is unable to be simply automated by a general-purpose computer. While it may be desired that a system for automatically identifying individuals for a cohort would identify the same or nearly the same individuals from a particular population as an abstractor, the automatic selection of individuals depends on specifically engineered technical capabilities designed to generate this result. On the other hand, in comparison to a manual process, automatic cohort selection may improve the cohort's quality as related to the cohort's contemplated use, because there may be fewer false positives or false negatives due to human error.

While automatic cohort selection may be accomplished in various ways, in some embodiments, such cohort selection may be made using a model. As used herein, a model may refer to a rules-based model (e.g., a model based on matching a set of search terms, regular expressions) or a trained model (e.g., a supervised machine learning system)).

A trained model (e.g., a supervised machine learning system) may use a framework based on a set of data labels, and may be trained to generate results consistent with that set of labels. In some cases, the trained model may be provided with a set of inputs (e.g., one or more feature vectors derived from patient medical records, which may be generated as part of the procedure to train the model) and may generate as an output a score or confidence level that may be used to determine if a particular individual may be omitted from a cohort or whether the individual may be an appropriate candidate for the cohort (e.g., based on comparison of the output to a predetermined threshold level).

The selection model may employ any suitable machine learning algorithms. In some embodiments, a logistic regression model may be used. Other types of machine learning techniques may also be used, either in combination with or separate from the logistic regression technique.

As discussed earlier, the disclosed systems and methods may select one or more cohorts via a rules-based model (e.g., a model based on a matching a set of search terms). For example, a rules-based model may receive data and generate output by matching at least a portion of the received data to a pre-defined set of search terms.

Training of the model may involve the use of a labeled data set for which a desired outcome is already known. Such data may be referred to as "reference standard" and may be generated, for example, through an abstraction process in which all of the individuals of a particular population are screened relative to one or more cohorts, and each individual is assigned to an appropriate cohort. Next, a certain percentage of the reference standard data (e.g., 50%, 60%, 70%, etc.) may be used to train the model. That is, the training segment may be analyzed (e.g., using natural language processing) such that feature vectors are extracted for each individual in the training segment. Those feature vectors may be provided to the model along with information about the desired outcome (e.g., whether a particular individual should be designated for a particular cohort). Through exposure to many such instances, the model may "learn" and provide outputs identical to or close to selections made through the abstraction process.

The remainder of the reference standard data may be used to test the trained model and evaluate its performance. For example, for each individual in the remainder of the reference standard data, feature vectors may be extracted from the medical records associated with that individual. Those feature vectors may be provided to the model, and the output of the model for that individual (and, indeed, for each individual in the remaining reference standard data) may be compared to the known outcome for that individual. If deviations are found between the model output and the known outcomes for any individuals, the deviations may be used to update the model (e.g., retrain the model). For example, one or more functions of the model may be added, removed, or modified, e.g., a quadratic function may be modified into a cubic function, an exponential function may be modified into a polynomial function, or the like. Accordingly, the deviations may be used to inform decisions to modify how the features passed into the model are constructed or which type of model is employed. Where the level of deviation is within a desired limit (e.g., 10%, 5%, or less), then the model may be deemed suitable for operating on a data set for which previous cohort selections have not been made. As an alternative, in some embodiments, one or more weights of the regression (or, if the model comprises a neural network, one or more weights of the nodes) may be adjusted to reduce the deviations.

Although described above using deviations, one or more loss functions may be used to measure the accuracy of the model. For example, a square loss function, a hinge loss functions, a logistic loss function, a cross entropy loss function, or any other loss function may be used. In such embodiments, the updates to the model may be configured to reduce (or even minimize, at least locally) the one or more loss functions.

In the process of analyzing a new set of data (e.g., patient medical records), various techniques may be used to provide feature vectors to the model (e.g., natural language processing techniques). In some instances, unstructured documents associated with a patient's medical record (e.g., an EMR) or in other available data sources (e.g., claims data, patient-reported data) may be analyzed for the presence of various words or phrases that may be associated with a particular cohort. For example, some or part of the documents of a patient's medical records may be available electronically. Alternatively, the typed, handwritten, or printed text in the records may be converted into machine-encoded text (e.g., through optical character recognition (OCR)), and the electronic text may be searched for certain key words or phrases associated with a particular cohort. If such words or phrases (e.g., "breast cancer," "metastatic," etc.) are identified in the records, then a snippet of text in a vicinity of the identified word or text may be tested to glean additional information about the context of the word or phrase. For example, "no evidence of metastatic activity" may convey a significantly different meaning from "stage IV; metastatic." By analyzing the snippet of text surrounding words or phrases of interest, one or more features may be extracted, forming a feature vector that may be provided as input to the trained selection model. These features from the unstructured documents may be combined with features from structured data associated with the patient's medical record or other available data sources (e.g., claims data, patient-reported data).

Analyzing snippets of text may allow for model generation that is significantly more efficient and less time consuming than analyzing every word/phrase included in a patient's medical history along with the context of the included words/phrases. For example, the number of dimensions may be greatly reduced by using snippets generated from relevant search terms rather than allowing the number of dimensions to expand to encompass all words, phrases, and structured data within a patient's medical history. In addition to increasing efficiency, this dimensionality reduction may further improve the accuracy of the generated model by easily preventing overfitting, which tends to occur when too many dependent variables are considered. Accordingly, analyzing snippets of text may result in better-performing models because such analyses tend to result in predictions that generalize to new datasets with fewer errors. Accordingly, human insights or expertise may help guide the feature extraction process to find more useful features than if the process examined all of the words across all of the records.

A system for automatic cohort selection may also be developed to mitigate potential negative effects from making cohort selections that are either under-inclusive or over-inclusive. Over-inclusion of individuals into a particular cohort may reduce the effectiveness of the cohort as an analytic or quality assessment tool, as the cohort may include one or more individuals not exhibiting the desired trait or characteristic associated with a particular cohort. For instance, an end user's analyses aimed at monitoring the effects of treatment protocols, etc., on the individuals in the cohort may be less useful if some of the members of the cohort lack the trait or characteristic at which the treatment protocol is directed. Under-inclusion may result in too few individuals in the cohort to provide a meaningful sample size. Under-inclusion, especially if based on a systematic exclusion of individuals, may also introduce bias into the cohort which can render the cohort less useful as an analytic tool.

The described model-assisted cohort selection system may include one or more tools to reduce or eliminate the effects of cohort bias. For example, in some cases, the model may be periodically re-trained as newly available reference data sets become available. Re-training may occur at any suitable time interval (e.g., daily, weekly, monthly, etc.). Such re-training may increase flexibility of the model and may render the model less susceptible to inadvertently omitting individuals from a cohort in which they would otherwise belong due to changes in how information about the individual is presented in an associated record (e.g., a terminology change, etc.). In other embodiments, the re-training may be based on new or updated reference standard data as they become available (e.g., through the abstraction process). Performing such updates periodically and at scale may help the model to continuously adapt and evolve to changes in the underlying data.

Additionally, the performance of the model-assisted cohort selection system may be continuously tested for a desired level of effectiveness and/or accuracy. For example, a random set of individuals excluded from a particular cohort may be processed via abstraction to verify the accuracy of the output of the model-assisted system. Such a process may allow for monitoring whether individuals are systematically excluded from a cohort—something that can result in undesirable biasing of the cohort, as explained above.

The system may also include one or more tools designed to quantify the quality of the cohort such that a human or machine may better detect bias, which in turn influences the quality of the cohort (e.g., as an analytic or quality assessment tool). For example, the system may output one or more measures of the cohort quality to a graphical user interface (or to any other suitable output platform).

System behavior and performance may be monitored against various metrics. In some instances, the sensitivity of the trained system may be monitored to determine whether the system is capturing all or substantially all of the individuals from a particular population that should be included in a particular cohort. Additionally, or alternatively, the efficiency of the system may be monitored to determine an achieved reduction (e.g., a percentage reduction) in the number of individuals required to proceed to an abstraction process. In some embodiments, the trained model may provide a sensitivity level of 95% or higher, meaning that less than 5% of individuals from a particular population that should be included in a particular cohort are omitted from the cohort. In some cases, the trained system may provide efficiency levels of 50% or more, meaning that half or less of a particular population would require abstraction subsequent to operation of the model-assisted cohort selector. Such efficiencies may be realized where the model-assisted system generates a confidence level or score high enough for certain individuals to conclude that those individuals do not belong in a particular cohort. In such instances, abstraction for those individuals may not be required. For the remaining individuals in a population not excluded from the cohort by the model-assisted selector, abstraction may be employed to confirm whether inclusion of those individuals into the cohort is appropriate.

The selection criteria of the model may be varied to achieve desired selectivity and/or efficiency levels. For example, where the selection criteria are made less rigorous, fewer individuals in a given population may be excluded from the cohort by the model-assisted system, and more cohort candidates may be identified. In such a case, the sensitivity may rise, as fewer individuals that should be included in the cohort would be lost from the cohort as a result of automatic selection. In such cases, however, the abstraction reduction efficiency may decline, as more individuals may be required to go through an abstraction process to confirm their placement into the cohort. On the other hand, if the selection criteria are made more rigorous, then more individuals could potentially be identified as inappropriate for the cohort. In such cases, the abstraction efficiency may rise, as few individuals would be required to proceed to an abstraction process. More rigorous selection criteria, however, may result in a reduction in sensitivity, meaning that the cohort may ultimately be under-inclusive.

Figure 5:
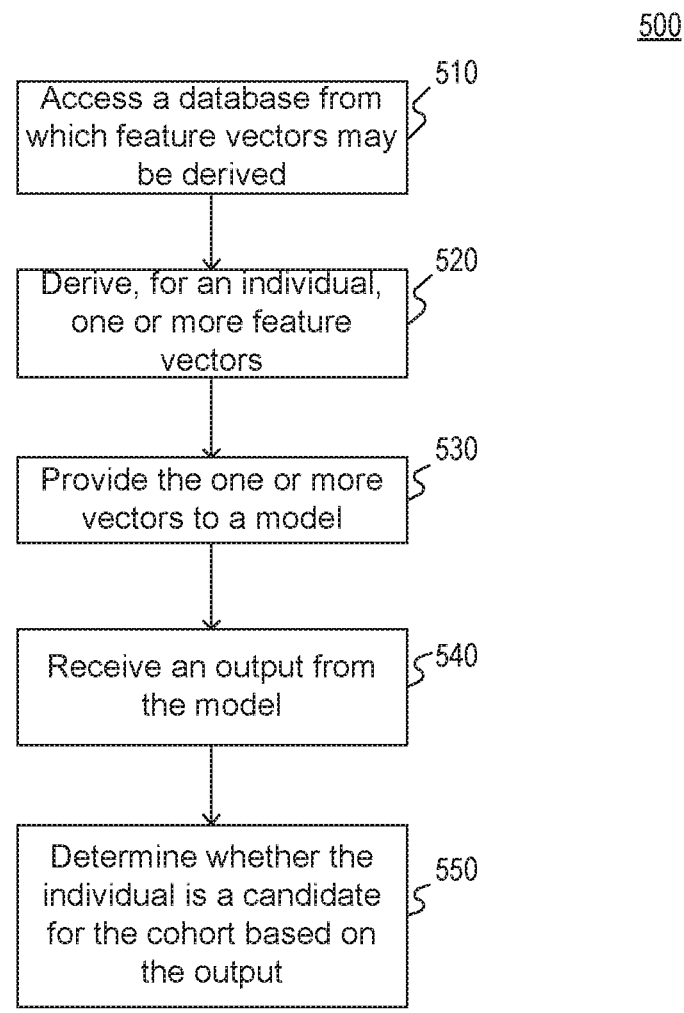
FIG. 5 is a flowchart illustrating an exemplary method for selecting a cohort from among a population of individuals consistent with the present disclosure.

FIG. 5 illustrates an exemplary method 500 for selecting a cohort from among a population of individuals. Method 500 may be implemented, for example, by processing engine 410 of system 400 of FIG. 4. Processing engine 410 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

At step 510, the at least one processing device may access, via a data interface, a database from which feature vectors associated with an individual from among a population of individuals can be derived. For example, the database may include a plurality of medical records, each record associated with a patient. The plurality of patients may include the individual. Some patients may include a single record while others many include a plurality of records.

As explained above with respect to FIG. 1, in some embodiments, the database may include a plurality of electronic data representations. For example, one or more electronic files, such as text files, image files, PDF files, XLM files, YAML files, or the like. In such embodiments, the at least one processing device may upload the plurality of electronic data representations via the data interface. In one example, as explained above, the electronic data representations may include electronic representations of documents from an electronic medical record associated with the individual. Additionally or alternatively, the electronic data representations may include at least some text previously subjected to an optical character recognition process. The plurality of electronic data representations may include both structured data and unstructured data. As explained above, "structured data" may comply with one or more standardized formats (e.g., a date format, a name format, or the like) and/or be stored in a serialized or marked-up format that includes labels or other indicators associated with portions of the data.

In embodiments where the database includes the plurality of electronic data representations, the plurality of electronic data representations may be derived from at least one of an electronic medical record (e.g., from a hospital, doctor's office, outpatient center, or the like), an available data source, claims data (e.g., from an insurance company), or patient-reported data associated with the at least one individual.

At step 520, the at least one processing device may derive, for the individual, one or more feature vectors from the database. For example, as explained above with respect to FIGS. 3A and 3B, one or more feature vectors may be extracted from the medical records using one or more relevant search terms. Snippet extraction may be used in combination with the relevant search terms in order to extract the feature vectors.

In embodiments where the database includes a plurality of electronic data representations, the at least one processing device may generate the one or more feature vectors using the plurality of electronic data representations. Additionally or alternatively, the at least one processing device may generate the one or more feature vectors by searching the plurality of electronic data representations for the presence of at least one term or phrase predetermined as associated with the cohort. After identifying the at least one term or phrase as present in the plurality of electronic data representations, the at least one processing device may extract a text grouping from the plurality of electronic data representations. The text grouping may include one or more words located in a vicinity of the identified term or phrase. The at least one processing device may generate the one or more feature vectors based on analysis of the identified term or phrase together with analysis of the extracted text grouping.

At step 530, the at least one processing device may provide the one or more feature vectors to a model. For example, the model may have been constructed as described above with respect to FIGS. 2A and 2B.

In some embodiments, the model may include a trained machine learning model. In such embodiments, the machine learning model may have been trained based on a set of structured information extracted by a combination of humans and machines from unstructured information, including a medical record. The machine learning model may comprise, for example, a neural network with a plurality of trained nodes, or the like.

Additionally or alternatively, the model may include a rules-based model. For example, the model may include a plurality of rules derived from logistic regression. In such embodiments, the rules-based model may generate output by matching a pre-defined set of search terms.

At step 540, the at least one processing device may receive an output from the model. For example, the output may comprise a score representing a possibility that the individual is viable for inclusion in the cohort. In embodiments where the cohort includes a plurality of sub-cohorts, the output may comprise a plurality of probabilities, scores, likelihoods, or the like for inclusion in each sub-cohort.

In some embodiments, the model may generate the output using a binary classification algorithm. For example, the binary classification may comprise a Boolean indicator of whether the individual is viable for the cohort. In such embodiments, the binary classification algorithm may include logistic regression, as explained above.

In some embodiments, the output received from the model may convey a confidence score. For example, as explained above, the confidence score may indicate a probability for inclusion in the cohort (or in a sub-cohort thereof).

At step 550, the at least one processing device may determine whether the individual from among the population of individuals is a candidate for the cohort based on the output received from the model. For example, the at least one processing device may select the individual if the output indicates that the individual is viable for the cohort.

In some embodiments, the cohort is to include individuals all sharing at least one medical or demographic characteristic. Accordingly, the output from the model may be based on the at least one medical or demographic characteristic. For example, the model may be configured to estimate the probability of metastatic cancer based on the feature vectors.

In embodiments where the output conveys a confidence score, the determination of whether the at least one individual is a candidate for the cohort may be based on a comparison of the confidence score to a predetermined threshold. The threshold may be adjustable based on desired levels of efficiency and performance. For example, as explained above, the model may be re-trained based on testing data (which may comprise records from the database not used to develop the model). One or more loss functions may be used to adjust the threshold.

Method 500 may further include additional steps. For example, method 500 may further include displaying an indicator of whether the individual is a candidate. The at least one processing device may send, via the data interface, a visualization of the indicator for display on a screen. For example, the visualization may comprise a user interface including the indicator. The visualization may be transmitted to one or more computing devices associated with a medical professional. The medical professional may be managing a medical test using the cohort.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A model-assisted selection system for identifying candidates for placement into a cohort, the system comprising:
   a data interface; and
   at least one processing device programmed to:
      receive, via the data interface, a selection of one or more relevant search terms from a user;
      receive, via the data interface, a plurality of medical records from a database storing records associated with selected individuals in a population of individuals, each of the selected individuals being associated with one or more of the medical records;
      extract, from the plurality of medical records, one or more snippets based on the one or more relevant search terms, each of the one or more snippets comprising a subset of text, within the plurality of records, surrounding the one or more relevant search terms and including a plurality of neighboring terms in addition to the one or more relevant search terms;
      derive, based on the one or more extracted snippets, one or more feature vectors associated with one or more of the plurality of medical records;
      provide the one or more feature vectors to a trained machine learning model;
      receive outputs from the model, the outputs comprising scores for ones of the selected individuals, the one or more feature vectors being associated with one or more of the medical records associated with the scored individuals; and
      determine whether the scored individuals are candidates for a cohort based on the received scores, wherein the determination is based on a comparison of each of the received scores to a predetermined threshold that is adjustable.

2. The system of claim 1, wherein the plurality of neighboring terms are after the one or more relevant search terms.

3. The system of claim 1, wherein the plurality of neighboring terms are before the one or more relevant search terms.

4. The system of claim 1, wherein the at least one processing device is further programmed to extract structured information from the plurality of records.

5. The system of claim 4, wherein the one or more feature vectors are further derived based on the extracted structured information.

6. The system of claim 1, wherein the one or more feature vectors further include values associated with the one or more relevant search terms, the values associated with the one or more relevant search terms representing a number of instances of the one or more relevant search terms in the plurality of records.

7. The system of claim 6, wherein the values associated with the one or more relevant search terms include a normalized representation of the number of instances.

8. A method for selecting a cohort from among a population of individuals, the method comprising:
   receiving, via a data interface, a selection of one or more relevant search terms from a user;
   receiving, via the data interface, a plurality of medical records from a database storing records associated with selected individuals in a population of individuals, each of the selected individuals being associated with one or more of the medical records;
   extracting, from the plurality of medical records, one or more snippets based on the one or more relevant search terms, each of the one or more snippets comprising a subset of text, within the plurality of records, surrounding the one or more relevant search terms and including a plurality of neighboring terms in addition to the one or more relevant search terms;
   deriving, based on the one or more extracted snippets, one or more feature vectors associated with one or more of the plurality of medical records;
   providing the one or more feature vectors to a trained machine learning model;
   receiving outputs from the model, the outputs comprising scores for ones of the selected individuals, the one or more feature vectors being associated with one or more of the medical records associated with the scored individuals; and
   determining whether the scored individuals are candidates for a cohort based on the received scores, wherein the determination is based on a comparison of each of the received scores to a predetermined threshold that is adjustable.

9. The method of claim 8, wherein the plurality of neighboring terms are after the one or more relevant search terms.

10. The method of claim 8, wherein the plurality of neighboring terms are before the one or more relevant search terms.

11. The method of claim 8, wherein the at least one processing device is further programmed to extract structured information from the plurality of records.

12. The method of claim 11, wherein the one or more feature vectors are further derived based on the extracted structure information.

13. The method of claim 8, wherein the one or more feature vectors further include values associated with the one or more relevant search terms, the values associated with the one or more relevant search terms representing a number of instances of the one or more relevant search terms in the plurality of records.

14. The method of claim 13, wherein the values associated with the one or more relevant search terms include a normalized representation of the number of instances.

15. A non-transitory computer-readable medium storing instructions that, when executed by at least one processing device, cause the at least one processing device to perform a method for selecting a cohort from among a population of individuals, the method comprising:
- receiving, via a data interface, a selection of one or more relevant search terms from a user;
- receiving, via the data interface, a plurality of medical records from a database storing records associated with selected individuals in a population of individuals, each of the selected individuals being associated with one or more of the medical records;
- extracting, from the plurality of medical records, one or more snippets based on the one or more relevant search terms, each of the one or more snippets comprising a subset of text, within the plurality of records, surrounding the one or more relevant search terms and including a plurality of neighboring terms in addition to the one or more relevant search terms;
- deriving, based on the one or more extracted snippets, one or more feature vectors associated with one or more of the plurality of medical records;
- providing the one or more feature vectors to a trained machine learning model;
- receiving outputs from the model, the outputs comprising scores for ones of the selected individuals, the one or more feature vectors being associated with one or more of the medical records associated with the scored individuals; and
- determining whether the scored individuals are candidates for a cohort based on the received scores, wherein the determination is based on a comparison of each of the received scores to a predetermined threshold that is adjustable.

* * * * *